United States Patent [19]

Gras et al.

[11] Patent Number: 5,494,994
[45] Date of Patent: Feb. 27, 1996

[54] SALTS OF PYROMELLITIC ACID, A PROCESS FOR THEIR PREPARATION AND THEIR USE

[75] Inventors: Rainer Gras, Bochum; Elmar Wolf, Recklinghausen, both of Germany

[73] Assignee: Huels Aktiengesellschaft, Marl, Germany

[21] Appl. No.: 365,115

[22] Filed: Dec. 28, 1994

[30] Foreign Application Priority Data

Jan. 14, 1994 [DE] Germany .......................... 44 00 928.3
Feb. 3, 1994 [DE] Germany .......................... 44 03 225.0

[51] Int. Cl.⁶ .................................................. C08G 69/08
[52] U.S. Cl. ............................. 528/292; 528/93; 528/94; 528/114; 528/117; 528/118; 528/119; 528/288; 528/289; 528/369; 525/438; 525/533; 525/934
[58] Field of Search ...................... 525/438, 533, 525/934; 528/93, 94, 114, 117, 118, 119, 288, 289, 292, 369

[56] References Cited

U.S. PATENT DOCUMENTS

| | | | |
|---|---|---|---|
| 3,277,052 | 10/1966 | Thompson et al. | 528/114 |
| 3,301,795 | 1/1967 | Wooster | 528/114 |
| 3,746,686 | 7/1973 | Marshall et al. | 528/114 |
| 3,944,598 | 3/1976 | Paustian et al. | 549/474 |
| 3,947,384 | 3/1976 | Schulde et al. | 525/423 |
| 4,007,299 | 2/1977 | Schulde et al. | 525/533 |
| 4,130,510 | 12/1978 | Tanaka et al. | 525/504 |
| 4,312,974 | 1/1982 | Chiao | 528/114 |
| 4,496,710 | 1/1985 | Gude et al. | 528/114 |

*Primary Examiner*—Melvyn I. Marquis
*Assistant Examiner*—Randy Gulakowski
*Attorney, Agent, or Firm*—Oblon, Spivak, McClelland, Maier & Neustadt

[57] ABSTRACT

The invention relates to new salts of pyromellitic acid, to a process for their preparation and to their use for the production of matt epoxide and hybrid powder coatings.

2 Claims, No Drawings

SALTS OF PYROMELLITIC ACID, A PROCESS FOR THEIR PREPARATION AND THEIR USE

BACKGROUND OF THE INVENTION

1. Field of the Invention

The invention relates to new salts of pyromellitic acid, to a process for their preparation and to their use for the production of matt epoxide and hybrid powder coatings.

2. Description of the Background

U.S. Pat. Nos. 4,007,299 and 3,947,384 describe processes for the production of matt coatings, in which epoxy resins are cured using salts of pyromellitic acid and cyclic amidines (imidazolines, tetrahydropyrimidines). However, no other salts of pyromellitic acid have been described to be suitable for the production of matt epoxy powder coatings.

SUMMARY OF THE INVENTION

Accordingly, one object of the present invention is to provide novel pyromellitic salts suitable for production of matt epoxy powder coatings and matt hybrid powder coatings.

The present inventors have now found that matt epoxy and hybrid powder coatings can be produced using salts of pyromellitic acid and various amines.

Accordingly, the present invention relates to salts of pyromellitic acid comprising pyromellitic acid and an amine component of the formula:

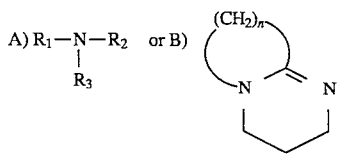

wherein for (A), $R_1$, $R_2$ and $R_3$, identical or different, are aliphatic, cycloaliphatic, araliphatic and/or aromatic hydrocarbon radicals having 1–20 carbon atoms, in which one or more $CH_2$ groups in the carbon chain can be replaced by O atoms, by $NR_4$ where $R_4$ is $C_{1-6}$-alkyl, or by CH—OH groups, and/or in which one or more terminal methyl groups can be replaced by dialkyl-substituted amino groups having 1 to 6 carbon atoms; or $R_1$ and $R_2$ may jointly form a ring in which a $CH_2$ group may be replaced by an O atom or by an $NR_4$ group; or $R_1$, $R_2$ and $R_3$ are —$CH_2$—$CH_2$-attached via a common N atom; and for (B), n is an integer of from 3 to 11.

DETAILED DESCRIPTION OF THE PREFERRED EMBODIMENTS

Pyromellitic acid, or 1,2,4,5-benzenetetracarboxylic acid, can be obtained commercially, for example from Aldrich (Milwaukee, Wis.).

Suitable amine compounds useful for preparing the salts of pyromellitic acid according to the invention are those capable of forming salts, for example N,N-dimethylcyclohexylamine, N,N-dimethylaniline, N-methylmorpholine, N,N'-dimethylpiperazine, 2,2,6,6-tetramethyl-4-dimethylaminopiperidine, N,N-dimethyloctadecylamine, N,N-dimethylhexadecylamine, 1,8-diazabicyclo[5.4.0]undec-7-ene, N,N,N',N'-tetramethylhexamethylenediamine and N,N,N', N',N"-pentamethyldiethylenetriamine.

The salts of pyromellitic acid according to the present invention have a basic nitrogen content of 1 to 10 mmol/g and a carboxyl group content of 3 to 13 mmol/g.

The salts of pyromellitic acid according to the present invention are substances which range from colourless to—in some cases—an intense yellow and having melting points of from 140° C. to about 250° C.

The salts of pyromellitic acid according to the present invention can be prepared in a known manner, for example by adding the amine component in portions to pyromellitic acid dissolved in water or ethanol at the boiling temperature. When the addition of amine is complete, heating is continued for about 1 hour more. The reaction mixture is then cooled to room temperature. The precipitate formed is filtered off and dried at from 60° to 80° in a vacuum drying cabinet.

In a second embodiment, the invention relates to a process for the preparation of salts of pyromellitic acid comprising reacting 1 mol of pyromellitic acid with 0.5 to 2 mol of amine (A) or (B) in $H_2O$ and/or ethanol at 50°–100° C. and, after the reaction has finished, isolating the reaction product from the solvent.

In a third embodiment, the invention relates to the use of salts of pyromellitic acid for the production of matt epoxide or hybrid powder coatings, the epoxy resin containing (i) 1 to 12% by weight, preferably 2 to 7% by weight, particularly preferably 3 to 5.5% by weight, of a salt of pyromellitic acid, (ii) COOH-containing polyesters and (iii) optionally, polyisocyanates. The above percentages by weight are based on the sum of epoxide plus COOH-containing polyesters which may be present plus any polyisocyanates which may additionally be present.

Suitable polyisocyanates include blocked polyisocyanates such as ε-caprolactam-blocked polyisocyanates and/or polyisocyanates which are free from blocking agents.

Suitable epoxide resins are solid, resinous substances which melt in the range 60° to 150° C., preferably 70° to 110° C. and which contain on average more than one 1,2-epoxide group per molecule. In principle, suitable compounds are all those containing more than on 1,2-epoxide group per molecule; preferably, however, commercially available epoxy resins are employed, as are obtained by reaction of bisphenol A and epichlorohydrin and having an epoxide equivalent weight of 400 to 3000, preferably 800 to 1000.

The COOH-containing polyesters are polyester-polycarboxylic acids which are prepared from polyols and polycarboxylic acids and/or their derivatives. The melting range of these acidic polyesters is in the range from 60 to 160° C preferably 80° to 120° C.; their acid number varies from 10 to 150 mg of KOH/g, preferably 30 to 60 mg of KOH/g. The OH numbers should be below 10 mg of KOH/g.

Suitable polycarboxylic acids employed for the preparation of the polyester-polycarboxylic acids include oxalic, adipic, 2,2,4-(2,4,4-trimethyladipic, azelaic, sebacic, decanedicarboxylic, dodecanedicarboxylic, fumaric, phthalic, isophthalic, terephthalic, trimellitic and pyromellitic acid. Suitable polyols useful as the acidic polyesters include: ethylene glycol, 1,2- and 1,3-propanediol, 1,2-, 1,3-, 1,4-and 2,3-butanediol, 1,5-pentanediol, 3-methyl-1,5-pentanediol, neopentylglycol, 1,6-hexanediol, 1,12-dodecanediol, 2,2,4-(2,4,4-)trimethyl-1,6-hexanediol, trimethylolpropane, glycerol, pentaerythritol, 1,4-bishydroxymethylcyclohexane, cyclohexane-1,4-diol, diethylene glycol, triethylene glycol and dipropylene glycol. It is of course also possible to react polyesters which contain hydroxyl groups, and which are prepared by known methods from polycarboxylic acids and polyols, with polycarboxylic acids and/or polycarboxylic acid anhydrides to give the polyester-polycarboxylic acids.

The quantities of the individual powder coating binder components can be varied substantially.

In the case where the commercially available epoxy resins based on bisphenol A (+ epichlorohydrin) are used exclusively, the concentration of curing agent is 3 to 12% by weight. In the case where mixtures of epoxy resins of the bisphenol A diglycidyl ester and COOH-containing polyester type are used, the proportion depends on the acid number of the carboxy polyester. For example, at an acid number of 30 to 50 mg of KOH/g the weight ratio of epoxy resin to carboxy polyester is usually from 60:40 to 80:20, preferably 70:30. The concentration of the pyromellitic salts according to the invention in these epoxy resin/carboxy polyester mixtures is 2 to 10% by weight.

Suitable powder coatings can be prepared by first mixing the binders together with the levelling agent, pigment and/or filler and the UV and oxidation stabilizers, and thereafter homogenizing the mixture in an extruder at about 80° to 130° C. as described in DE 3328130. The extrudate is cooled to room temperature and then ground to give a powder coating whose average particle size is preferably about 40 to 80 μm, particularly preferably 50 μm.

When present, the isophorone diisocyanate adducts blocked with ε-caprolactam is used in amounts 0.1 to 0.5 NCO equivalents per 1 OH equivalent of the epoxy resin. Any solid (cyclo)aliphatic polyisocyaates can be used in accordance with the present invention as polyisocyanates. The solid, blocked as well as unblocked polyol-isophorone diisocyanate adducts (OH: NCO=1:2) as well as the trimeric (isocyanurate) of isophorone diisocyanate are particularly suitable. The mean molar weight of the polyisocyanate is 450 to 1,200, preferably 800 to 1,000.

The application of the powder coatings produced in this way to appropriate substrates can be carried out by the known processes, for example by electrostatic powder spraying or fluidized-bed sintering. Following the application of the powder coating by one of the processes mentioned, the coated substrates are heated at temperatures of 150° to 220° C. for periods of 8 to 30 min for purposes of curing. The coating films produced in this way are distinguished by very good levelling, outstanding solvent resistance and a matt surface of which it is possible to adjust the degree of gloss as desired within a wide range.

Having generally described this invention, a further understanding can be obtained by reference to certain specific examples which are provided herein for purposes of illustration only and are not intended to be limiting unless otherwise specified.

EXAMPLES

I. Preparation of the salts according to the invention
General preparation procedures
The salts of pyromellitic acid listed in the following table were prepared as follows:

a) The amine was added in portions to the pyromellitic acid dissolved in ethanol. After the addition of amine was complete, heating was continued for about 1 h more (at 60° C.). The mixture was then cooled to room temperature. The precipitate formed was filtered off and was dried at 60° C. in a vacuum drying cabinet in order to remove the ethanol completely.

b) The amine was added dropwise to the pyromellitic acid dissolved in water. After the addition of amine was complete, heating was continued for about 1 h more (at 60°–80° C.) and then the water was distilled off. For the complete removal of the water, drying was carried out at 80° C. in a vacuum drying cabinet.

| Example | Pyromelliric acid (mol) | (mol) | Amine | Melting range (°C.) | $NH_2$ mmol (g) | COOH mmol (g) |
|---|---|---|---|---|---|---|
| 1 | 1 | 1 | 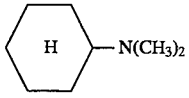 H—⟨⟩—N(CH$_3$)$_2$ | 188–197 | 2.601 | 10.263 |
| 2 | 1 | 2 | 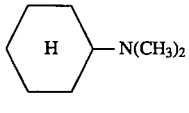 H—⟨⟩—N(CH$_3$)$_2$ | 192–201 | 3.865 | 7.923 |
| 3 | 1 | 1 | $(CH_3)_2N$—$C_{16}H_{33}$ | 195–215 | 1.892 | 7.557 |
| 4 | 1 | 1 | 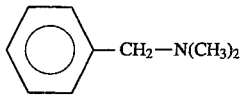 ⟨⟩—$CH_2$—$N(CH_3)_2$ | 184–189 | 2.5112 | 10.051 |
| 5 | 1 | 1 | $(CH_3)_2$—N—$C_{18}H_{37}$ | 191–206 | 1.801 | 7.196 |
| 6 | 1 | 1 | 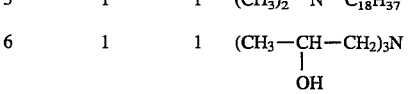 $(CH_3$—CH—$CH_2)_3N$<br>\|<br>OH | 165–179 | 2.210 | 8.814 |
| 7 | 1 | 1 | $(CH_3)_2$—N—$(CH_2)_2$—OH | 176–192 | 2.901 | 11.592 |

-continued

| Example | Pyromelliric acid (mol) | (mol) | Amine | Melting range (°C.) | $NH_2$ mmol (g) | COOH mmol (g) |
|---|---|---|---|---|---|---|
| 8  | 1 | 1   | O⟨ ⟩N—CH$_3$ (morpholine, N-methyl) | 225–229 | 2.917 | 11.166 |
| 9  | 1 | 2   | O⟨ ⟩N—CH$_3$ | 190–196 | 4.349 | 8.800 |
| 10 | 1 | 1   | HN⟨ ⟩H—N(CH$_3$)$_2$ | 226–237 | 4.466 | 9.032 |
| 11 | 1 | 1   | [O⟨ ⟩N—CH$_2$—CH$_2$]$_2$O | 120–129 | 9.105 | 9.200 |
| 12 | 1 | 1   | pyridine | 231–238 | 2.765 | 11.520 |
| 13 | 1 | 1   | ⟨ ⟩N—C$_2$H$_5$ | 223–230 | 2.719 | 10.678 |
| 14 | 1 | 2   | ⟨ ⟩N—CH$_3$ | 188–195 | 2.825 | 11.002 |
| 15 | 1 | 0.5 | >N—(CH$_2$)$_2$—N(CH$_3$)—(CH$_2$)$_2$—N< | 176–183 | 3.348 | 11.667 |
| 16 | 1 | 1   | >N—(CH$_2$)$_2$—N(CH$_3$)—(CH$_2$)$_2$—N< | 180–185 | 4.562 | 9.301 |
| 17 | 1 | 0.5 | >N—(CH$_2$)$_6$—N< | 217–222 | 2.870 | 11.664 |
| 18 | 1 | 1   | >N—(CH$_2$)$_6$—N< | 225–234 | 4.544 | 9.373 |
| 19 | 1 | 0.5 | >N—(CH$_2$)$_2$—N< | 227–234 | 2.915 | 12.431 |
| 20 | 1 | 1   | >N—(CH$_2$)$_2$—N< | 236–243 | 4.960 | 10.633 |
| 21 | 1 | 1   | N⟨ ⟩N (tetrahydropyrimidine) | 210–218 | 2.393 | 8.751 |
| 22 | 1 | 2   | N⟨ ⟩N | 160–180 | 3.304 | 7.018 |

-continued

| Example | Pyromelliric acid (mol) | (mol) | Amine | Melting range (°C.) | NH$_2$ mmol (g) | COOH mmol (g) |
|---|---|---|---|---|---|---|
| 23 | 1 | 1 | CH$_3$—N(piperazine)N—CH$_3$ | 258–270 | 2.690 | 10.712 |
| 24 | 1 | 1 | (tetrahydropyrimidine fused ring) | 206–215 | 2.461 | 9.965 |
| 25 | 1 | 1 | (piperazine) N N | >300 | 2.621 | 10.781 |
| 26 | 1 | 0.5 | H—(cyclohexyl)—N(CH$_3$)$_2$ | 180–190 | 2.631 | 10.313 |
|  |  | 0.5 | (N—CH$_3$ piperidine) |  |  |  |
| 27 | 1 | 0.5 | H—(cyclohexyl)—N(CH$_3$)$_2$ | 186–195 | 2.456 | 9.431 |
|  |  | 0.5 | (tetrahydropyrimidine) |  |  |  |
| 28 | 1 | 0.5 | H—(cyclohexyl)—N(CH$_3$)$_2$ | 178–186 | 2.753 | 10.715 |
|  |  | 0.5 | O(morpholine)N—CH$_3$ |  |  |  |

II. Epoxy resins

In the application examples the epoxy rein compounds employed were those based on bisphenol A. They have the following characteristics:

| Characteristics | Example II.1 | Example II.2 |
|---|---|---|
| equivalent weight | 900–1,000 | 1,700–2,000 |
| epoxide value | 0.1–0.111 | 0.05–0.058 |
| hydroxyl value | 0.34 | 0.36 |
| melting range °C. | 96–104 | 125–132 |

III. Epoxy resin powder coatings

In order to produce the powder coatings the ground products, curing agents, epoxy resin and levelling agent masterbatch[1] were intimately mixed with the white pigment (TiO$_2$) in an edge runner mill and then homogenized in an extruder at from 90° to 120° C. After cooling, the extrudate was fractionated and ground in a pin mill to a particle size <100 µm. The powder thus prepared was applied, using an electrostatic powder spraying unit at 60 kV, to degreased and —if appropriate—pretreated steel panels which were baked in a circulating-air laboratory drying cabinet.

[1] Levelling agent masterbatch 10% by weight of levelling agent based on polymeric butyl acrylates is homogenized in the melt with the epoxy resins and comminuted after solidifying.

The abbreviates in the following tables denote:

LT=Layer thickness (µm)

EI=Erichsen indentation (mm) (DIN 43 156)

CH=Cross hatch test (DIN 53 151)

GG 60° ≮=Gardner gloss (ASTM-D 523)

Imp. rev.=Impact reverse ( g·m )

MEK (methyl ethyl ketone) resistance: Number of strokes with an MEK-impregnated cotton-wool pad under a load of 1 kg until the coating surface is attacked.

EXAMPLE 1

In accordance with the method described, the powder coating with the formulation below was produced, applied and baked at between 200° C. and 180° C.

500.0 parts by weight of epoxide according to II.1
50.0 parts by weight of crosslinking agent according to I.1
400.0 parts by weight of white pigment (TiO$_2$)
50.0 parts by weight of levelling agent masterbatch

| Baking Conditions | | Mechanical Characteristics | | | | | | Solvent resistance |
|---|---|---|---|---|---|---|---|---|
| Time/min | Temp. °C. | LT | HB | Imp. rev. | EI | CH | GG 60° ≮ | MEK Resistance |
| 15 | 200 | 60–65 | 100 | <115.2 | 3.0–3.5 | 0 | 10 | 10 |
| 20 | | 70–75 | 100 | 115.2 | 5.2–6.5 | 0 | 10 | 12 |
| 25 | | 70–80 | 100 | 230.4 | 5.0–5.5 | 0 | 10 | 16 |
| 30 | 180 | 50–60 | 100 | 115.2 | 4.7–4.9 | 0 | 9 | 10 |

EXAMPLE 2

In accordance with the method described, the powder coating having the following formulation was produced, applied and baked at between 170° C. and 220° C.

480.0 parts by weight of epoxide according to II.1
70.0 parts by weight of crosslinking agent according to I.1
400.0 parts by weight of white pigment (TiO$_2$)
50.0 parts by weight of levelling agent masterbatch

| Baking Conditions | | Mechanical Characteristics | | | | | | Solvent resistance |
|---|---|---|---|---|---|---|---|---|
| Time/min | Temp. °C. | LT | HB | Imp. rev. | EI | CH | GG 60° ≮ | MEK Resistance |
| 6 | 220 | 60–80 | 111 | 230.4 | 5.5–6.0 | 0 | 18 | 70 |
| 12 | 200 | 70–90 | 111 | 345.6 | 5.3–5.9 | 0 | 20 | 80 |
| 15 | | 70–80 | 111 | 460.8 | 6.5–6.7 | 0 | 18 | 90 |
| 20 | | 60–80 | 111 | 576 | 6.5–7.6 | 0 | 18 | 100 |
| 15 | 180 | 70 | 100 | 115.2 | 3.4–4.2 | 0 | 19 | 60 |
| | | 65–90 | 111 | 115.2 | 4.5–4.9 | 0 | 20 | 70 |
| 25 | 170 | 70–80 | 100 | 115.2 | 4.1–4.4 | 0 | 18 | 30 |

EXAMPLE 3

In accordance with the method described, the powder coating with the following formulation was produced, applied and baked at between 200° C. and 180° C.

470.0 parts by weight of epoxide according to II.1
80.0 parts by weight of crosslinking agent according to I.1
400.0 parts by weight of white pigment (TiO$_2$)
50.0 parts by weight of levelling agent masterbatch

| Baking Conditions | | Mechanical Characteristics | | | | | | Solvent resistance |
|---|---|---|---|---|---|---|---|---|
| Time/min | Temp. °C. | LT | HB | Imp. rev. | EI | CH | GG 60° ≮ | MEK Resistance |
| 10 | 200 | 60 | 100 | 460.8 | 4.6–4.9 | 0 | 21 | 70 |
| 12 | | 60–80 | 100 | 460.8 | 5.1–5.8 | 0 | 20 | 80 |
| 15 | | 50–60 | 111 | 576 | 6.0–6.3 | 0 | 19 | 100 |
| 15 | 180 | 70 | 111 | 230.4 | 4.4–4.6 | 0 | 22 | 60 |
| 20 | | 70–80 | 111 | 345.6 | 4.7–5.3 | 0 | 21 | 70 |

EXAMPLE 4

In accordance with the method described, the powder coating having the following formulation was produced, applied and baked at between 200° C. and 180° C.

495.0 parts by weight of epoxide according to II.1
55.0 parts by weight of crosslinking agent according to I.3
400.0 parts by weight of white pigment (TiO$_2$)
50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ≮ | MEK Resistance |
| 20 | 200 | 60–80 | 100 | <115.2 | 2.7–4.1 | 0 | 21 | 8 |
| 25 | | 50–65 | 100 | 115.2 | 4.2–4.8 | 0 | 19 | 10 |
| 30 | | 70–80 | 100 | 115.2 | 5.6–6.2 | 0 | 19 | 10 |
| 30 | 180 | 70–80 | 100 | <115.2 | 3.8–4.5 | 0 | 26 | 8 |

EXAMPLE 5

In accordance with the method described, the powder coating having the following formulation was produced, applied and baked at between 180° C. and 200° C.

485.0 parts by weight of epoxide according to II.1
65.0 parts by weight of crosslinking agent according to I.3
400.0 parts by weight of white pigment (TiO$_2$)
50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ≮ | MEK Resistance |
| 20 | 200 | 70–80 | 100 | 115.2 | 5.6–5.7 | 0 | 18 | 10 |
| 25 | | 50–60 | 100 | 345.6 | 6.1–6.7 | 0 | 20 | 12 |
| 30 | | 70–80 | 100 | 345.6 | 6.2 | 0 | 20 | 12 |
| 25 | 180 | 70–80 | 100 | <115.2 | 2.6–3.5 | 0 | 20 | 8 |
| 30 | | 65–80 | 100 | 115.2 | 3.3–3.9 | 0 | 21 | 10 |

EXAMPLE 6

In accordance with the method described, the powder coating having the following formulation was produced, applied and baked at between 200° C. and 180° C.

490.0 parts by weight of epoxide according to II.1
60.0 parts by weight of crosslinking agent according to I.4
400.0 parts by weight of white pigment (TiO$_2$)
50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ≮ | MEK Resistance |
| 15 | 200 | 60–70 | 111 | 115.2 | 5.3–5.9 | 0 | 17 | 10 |
| 20 | | 60 | 111 | 115.2 | 6.0–6.4 | 0 | 19 | 14 |
| 25 | | 70–75 | 111 | 230.4 | 6.3–6.8 | 0 | 15 | 16 |
| 25 | 180 | 55–70 | 111 | 115.2 | 4.5–5.1 | 0 | 20 | 10 |
| 30 | | 60–70 | 111 | 230.4 | 5.3–5.8 | 0 | 21 | 14 |

EXAMPLE 7

In accordance with the method described, the powder coating having the following formulation was produced, applied and baked at between 200° C. and 180° C.

480.0 parts by weight of epoxide according to II.1
70.0 parts by weight of crosslinking agent according to I.4
400.0 parts by weight of white pigment (TiO$_2$)
50.0 parts by weight of levelling agent masterbatch

| Baking Conditions | | Mechanical Characteristics | | | | | Solvent resistance |
|---|---|---|---|---|---|---|---|
| Time/ min | Temp. °C. | LT | HB | Imp. rev. | EI | CH | GG 60° ≮ | MEK Resistance |
| 12 | 200 | 55–60 | 125 | 115.2 | 6.8–7.2 | 0 | 19 | 12 |
| 15 | | 50–65 | 125 | 115.2 | 6.3–6.6 | 0 | 18 | 18 |
| 20 | | 65–70 | 125 | 345.6 | 6.0–6.6 | 0 | 19 | 26 |
| 20 | 180 | 60–70 | 111 | 115.2 | 5.1–5.2 | 0 | 20 | 10 |
| 30 | | 60 | 125 | 230.4 | 5.0–5.5 | 0 | 19 | 18 |

EXAMPLE 8

In accordance with the method described, the powder coating having the following formulation below was produced, applied and baked at between 200° C. and 180° C.

470.0 parts by weight of epoxide according to II.1
80.0 parts by weight of crosslinking agent according to I.4
400.0 parts by weight of white pigment (TiO$_2$)
50.0 parts by weight of levelling agent masterbatch

| Baking Conditions | | Mechanical Characteristics | | | | | Solvent resistance |
|---|---|---|---|---|---|---|---|
| Time/ min | Temp. °C. | LT | HB | Imp. rev. | EI | CH | GG 60° ≮ | MEK Resistance |
| 12 | 200 | 60 | 111 | 230.4 | 6.3–7.9 | 0 | 25 | 24 |
| 15 | | 50–55 | 125 | 115.2 | 7.6–8.7 | 0 | 24 | 30 |
| 20 | | 65 | 125 | 345.6 | 7.0–7.6 | 0 | 26 | 36 |
| 20 | 180 | 60–70 | 111 | 115.2 | 5.6–5.9 | 0 | 26 | 18 |
| 30 | | 50–60 | 125 | 230.4 | 5.7–6.1 | 0 | 25 | 26 |

EXAMPLE 9

In accordance with the method described, the powder coating having the following formulation below was produced, applied and baked at between 200° C. and 180° C.

480.0 parts by weight of epoxide according to II.1
70.0 parts by weight of crosslinking agent according to I.5
400.0 parts by weight of white pigment (TiO$_2$)
50.0 parts by weight of levelling agent masterbatch

| Baking Conditions | | Mechanical Characteristics | | | | | Solvent resistance |
|---|---|---|---|---|---|---|---|
| Time/ min | Temp. °C. | LT | HB | Imp. rev. | EI | CH | GG 60° ≮ | MEK Resistance |
| 20 | 200 | 50–60 | 100 | 115.2 | 5.2–5.6 | 0 | 19 | 10 |
| 25 | | 60 | 100 | 115.2 | 5.9–6.3 | 0 | 21 | 12 |
| 30 | | 55–60 | 100 | 230.4 | 6.0–6.2 | 0 | 20 | 14 |
| 30 | 180 | 60–65 | 100 | 115.2 | 4.1–4.9 | 0 | 22 | 10 |

EXAMPLE 10

In accordance with the method described, the powder coating having the following formulation below was produced, applied and baked at between 200° C. and 180° C.

220.0 parts by weight of epoxide according to II.1
260.0 parts by weight of epoxide according to II.2
70.0 parts by weight of crosslinking agent according to I.5
400.0 parts by weight of white pigment (TiO$_2$) 50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ⋠ | MEK Resistance |
| 12 | 200 | 60–70 | 111 | 230.4 | 5.1–5.7 | 0 | 19 | 70 |
| 15 |  | 60 | 100 | 345.6 | 5.9–6.4 | 0 | 21 | 80 |
| 20 |  | 60–65 | 111 | 460.8 | 6.3–6.9 | 0 | 20 | 88 |
| 15 | 180 | 55–65 | 100 | 115.2 | 3.6–4.0 | 0 | 18 | 56 |
| 20 |  | 60–70 | 111 | 115.2 | 4.3–4.7 | 0 | 20 | 64 |

EXAMPLE 11

In accordance with the method described, the powder coating having the following formulation below was produced, applied and baked at between 180° C. and 220° C.

490.0 parts by weight of epoxide according to II.1
60.0 parts by weight of crosslinking agent according to I.8
400.0 parts by weight of white pigment (TiO$_2$)
50.0 parts by weight of levelling agent masterbatch 480.0 parts by weight of epoxide according to II.1
70.0 parts by weight of crosslinking agent according to I.8
400.0 parts by weight of white pigment (TiO$_2$)
50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ⋠ | MEK Resistance |
| 10 | 220 | 50–60 | 100 | 115.2 | 3.8–4.2 | 0 | 10 | 24 |
| 20 | 200 | 45–60 | 111 | <115.2 | 3.1 | 0 | 9 | 24 |
| 25 |  | 60 | 111 | <115.2 | 3.2–3.4 | 0 | 9 | 26 |
| 30 |  | 50–60 | 100 | 115.2 | 4.0–5.7 | 0 | 10 | 30 |
| 30 | 180 | 60 | 100 | <115.2 | 3.1–3.5 | 0 | 9 | 24 |

EXAMPLE 12

In accordance with the method described, the powder coating having the following formulation below was produced, applied and baked at between 180° C. and 220° C.

485.0 parts by weight of epoxide according to II.1
65.0 parts by weight of crosslinking agent according to I.8
400.0 parts by weight of white pigment (TiO$_2$)
50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ⋠ | MEK Resistance |
| 10 | 220 | 60–70 | 125 | 115.2 | 4.7–5.6 | 0 | 14 | 24 |
| 20 | 200 | 40–60 | 125 | 115.2 | 5.8–6.1 | 0 | 13 | 28 |
| 25 |  | 60–80 | 125 | 115.2 | 5.7–6.4 | 0 | 15 | 32 |
| 30 |  | 60–70 | 125 | 230.4 | 5.8–6.5 | 0 | 13 | 36 |
| 25 | 180 | 60–75 | 125 | <115.2 | 4.5–5.8 | 0 | 13 | 20 |
| 30 |  | 40–50 | 125 | 115.2 | 6.0–6.6 | 0 | 15 | 26 |

EXAMPLE 13

In accordance with the method described, the powder coating having the following formulation below was produced, applied and baked at between 180° C. and 220° C.

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ⋖ | MEK Resistance |
| 10 | 220 | 60–70 | 111 | 115.2 | 4.0–4.5 | 0 | 21 | 40 |
| 15 | 200 | 50–60 | 111 | 115.2 | 4.2–5.7 | 0 | 22 | 38 |
| 20 | | 60 | 125 | 115.2 | 4.9–5.7 | 0 | 24 | 44 |
| 25 | | 60–85 | 125 | 230.4 | 5.0–5.9 | 0 | 24 | 50 |
| 25 | 180 | 60 | 111 | <115.2 | 4.1–4.2 | 0 | 21 | 28 |
| 30 | | 60–70 | 111 | 115.2 | 4.6–4.9 | 0 | 21 | 30 |

EXAMPLE 14

In accordance with the method described, the powder coating having the following formulation below was produced, applied and baked at between 170° C. and 220° C.

475.0 parts by weight of epoxide according to II.1

75.0 parts by weight of crosslinking agent according to I.8

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ⋖ | MEK Resistance |
| 10 | 220 | 60–75 | 111 | 115.2 | 5.1–5.5 | 0 | 32 | 70 |
| 15 | 200 | 60–65 | 111 | 115.2 | 5.2–5.7 | 0 | 32 | 70 |
| 20 | | 60–70 | 111 | 115.2 | 6.2–6.6 | 0 | 31 | 80 |
| 25 | | 60–75 | 111 | 230.4 | 5.8–6.0 | 0 | 32 | 90 |
| 20 | 180 | 50–80 | 111 | 115.2 | 5.2–6.3 | 0 | 32 | 70 |
| 25 | | 70–90 | 111 | 115.2 | 4.2–5.6 | 0 | 28 | 80 |
| 25 | 170 | 50–70 | 111 | <115.2 | 4.2–4.6 | 0 | 26 | 60 |

EXAMPLE 15

In accordance with the method described, the powder coating having the following formulation below was produced, applied and baked at 200° C.

480.0 parts by weight of epoxide according to II.1

70.0 parts by weight of crosslinking agent according to I.9

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ⋖ | MEK Resistance |
| 12 | 200 | 65–70 | 111 | <115.2 | 2.5–3.1 | 0 | 14 | 10 |
| 15 | | 60–65 | 111 | 115.2 | 3.9–4.3 | 0 | 15 | 16 |
| 20 | | 65–70 | 111 | 230.4 | 4.1–4.8 | 0 | 14 | 24 |

EXAMPLE 16

In accordance with the method described, the powder coating having the following formulation was produced, applied and baked at between 200° C. and 180° C.

480.0 parts by weight of epoxide according to II.1

70.0 parts by weight of crosslinking agent according to I.10

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 15 | 200 | 50–60 | 111 | 115.2 | 5.3–6.5 | 0 | 19 | 8 |
| 20 | | 60–70 | 111 | 115.2 | 7.3–7.5 | 0 | 20 | 10 |
| 25 | | 65–70 | 111 | 230.4 | 7.4–7.7 | 0 | 21 | 16 |
| 30 | 180 | 45–55 | 111 | 115.2 | 4.5–5.5 | 0 | 20 | 10 |

EXAMPLE 17

In accordance with the method described, the powder coating having the following formulation was produced, applied and baked at between 200° C. and 180° C.

480.0 parts by weight of epoxide according to II.1
70.0 parts by weight of crosslinking agent according to I.15
400.0 parts by weight of white pigment (TiO$_2$)
50.0 parts by weight of levelling agent masterbatch 485.0 parts by weight of epoxide according to II.1
65.0 parts by weight of crosslinking agent according to I.16
400.0 parts by weight of white pigment (TiO$_2$)
50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 10 | 200 | 60–70 | 125 | 115.2 | 4.0–4.2 | 0 | 17 | 50 |
| 15 | | 40–45 | 100 | 345.6 | 7.3–7.6 | 0 | 16 | 120 |
| 20 | | 50–60 | 111 | 230.4 | 7.2–7.3 | 0 | 15 | 140 |
| 20 | 180 | 70–90 | 111 | 115.2 | 3.9–5.0 | 0 | 20 | 22 |
| 25 | | 50–60 | 100 | 115.2 | 4.5–4.8 | 0 | 20 | 46 |

EXAMPLE 18

In accordance with the method described, the powder coating having the following formulation was produced, applied and baked at between 200° C. and 180° C.

490.0 parts by weight of epoxide according to II.1
60.0 parts by weight of crosslinking agent according to I.15
400.0 parts by weight of white pigment (TiO$_2$)
50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 15 | 200 | 50–60 | 111 | 115.2 | 4.1–4.4 | 0 | 20 | 40 |
| 20 | | 60–70 | 100 | 230.4 | 6.0–6.4 | 0 | 18 | 80 |
| 25 | | 50–60 | 111 | 230.4 | 6.3–6.9 | 0 | 20 | 110 |
| 25 | 180 | 55–65 | 111 | 115.2 | 4.0–4.8 | 0 | 21 | 18 |
| 30 | | 50–60 | 100 | 115.2 | 4.7–5.1 | 0 | 19 | 48 |

EXAMPLE 19

In accordance with the method described, the powder coating having the following formulation was produced, applied and baked at between 180° C. and 220° C.

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 10 | 220 | 50–60 | 100 | 115.2 | 3.5–4.1 | 0 | 11 | 26 |
| 15 | 200 | 45–55 | 100 | <115.2 | 3.8–4.0 | 0 | 10 | 28 |
| 20 |  | 45–60 | 100 | 115.2 | 3.5–3.7 | 0 | 10 | 28 |
| 25 |  | 60–70 | 111 | 115.2 | 3.8–4.5 | 0 | 10 | 30 |
| 30 | 180 | 45–60 | 111 | <115.2 | 3.0–3.9 | 0 | 13 | 22 |

EXAMPLE 20

In accordance with the method described, the powder coating having the following formulation was produced, applied and baked at between 200° C.

480.0 parts by weight of epoxide according to II.1

70.0 parts by weight of crosslinking agent according to I.17

400.0 parts by weight of white pigment (TiO$_2$)

50.0 parts by weight of levelling agent masterbatch 75.0 parts by weight of crosslinking agent according to I.18

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 15 | 200 | 60–55 | 111 | 230.4 | 7.0 | 0 | 18 | 100 |
| 20 |  | 55–60 | 111 | 230.4 | 6.5–6.8 | 0 | 18 | 140 |

EXAMPLE 21

In accordance with the method described, the powder coating having the following formulation was produced, applied and baked at between 200° C. and 180° C.

490.0 parts by weight of epoxide according to II.1

60.0 parts by weight of crosslinking agent according to I.17

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 15 | 200 | 50–60 | 111 | 115.2 | 5.9–6.5 | 0 | 16 | 40 |
| 20 |  | 55–65 | 111 | 230.4 | 6.3–6.9 | 0 | 14 | 82 |
| 30 | 180 | 50–55 | 100 | 115.2 | 4.9–5.5 | 0 | 15 | 56 |

EXAMPLE 22

In accordance with the method described, the powder coating having the following formulation was produced, applied and baked at between 180° C. and 200° C.

475.0 parts by weight of epoxide according to II.1

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 15 | 200 | 60 | 100 | 460.8 | 3.4–4.0 | 0 | 7 | 22 |
| 20 | | 45–60 | 100 | 460.8 | 5.0–5.2 | 0 | 7 | 40 |
| 25 | | 50–60 | 100 | 460.8 | 5.3–5.6 | 0 | 7 | 50 |
| 25 | 180 | 55–65 | 100 | 115.2 | 3.3–3.4 | 0 | 11 | 10 |
| 30 | | 50–60 | 100 | 115.2 | 4.4–4.6 | 0 | 12 | 20 |

EXAMPLE 23

In accordance with the method described, the powder coating having the following formulation was produced, applied and baked at between 200° C. and 180° C.

260.0 parts by weight of epoxide according to II.1

220.0 parts by weight of epoxide according to II.1

70.0 parts by weight of crosslinking agent according to I.18

400.0 parts by weight of white pigment (TiO$_2$)

50.0 parts by weight of levelling agent masterbatch 50.0 parts by weight of crosslinking agent according to I.18

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 15 | 200 | 50–60 | 100 | 230.4 | 3.7–4.1 | 0 | 9 | 20 |
| 20 | | 55–70 | 111 | 230.4 | 4.9–5.5 | 0 | 10 | 28 |
| 25 | | 60–70 | 100 | 345.6 | 5.2–5.6 | 0 | 9 | 46 |
| 25 | 180 | 60 | 100 | 115.2 | 3.2–3.6 | 0 | 12 | 10 |
| 30 | | 60–70 | 100 | 115.2 | 4.3–4.8 | 0 | 12 | 18 |

EXAMPLE 24

In accordance with the method described, the powder coating having the following formulation was produced, applied and baked at between 180° C. and 200° C.

485.0 parts by weight of epoxide according to II.1

65.0 parts by weight of crosslinking agent according to I.18

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 20 | 200 | 50–55 | 100 | 115.2 | 3.1–4.0 | 0 | 6 | 20 |
| 25 | | 50–65 | 100 | 230.4 | 5.2 | 0 | 6 | 24 |
| 30 | | 50–60 | 100 | 691.2 | 5.3–6.0 | 0 | 6 | 26 |
| 25 | 180 | 50–70 | 100 | <115.2 | 3.6–4.0 | 0 | 12 | 8 |
| 30 | | 50–55 | 100 | 115.2 | 4.5–5.4 | 0 | 12 | 14 |

EXAMPLE 25

In accordance with the method described, the powder coating having the following formulation was produced, applied and baked at between 180° C. and 200° C.

500.0 parts by weight of epoxide according to II.1

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ≮ | MEK Resistance |
| 20 | 200 | 40–50 | 100 | <115.2 | 2.8–3.8 | 0 | 5 | 12 |
|  |  | 50–65 | 100 | 115.2 | 5.1–5.5 | 0 | 6 | 18 |
| 30 |  | 40 | 100 | 115.2 | 6.3–6.6 | 0 | 6 | 20 |
| 20 | 180 | 50–60 | 100 | <115.2 | 4.0 | 0 | 12 | 8 |
| 25 |  |  |  |  |  |  |  |  |
| 30 |  | 50–60 | 10 | 115.2 | 4.4–4.6 | 0 | 12 | 10 |

EXAMPLE 26

In accordance with the method described, the powder coating having the following formulation was produced, applied and baked at between 200° C. and 180° C.

480.0 parts by weight of epoxide according to II.1

70.0 parts by weight of crosslinking agent according to I.19

400.0 parts by weight of white pigment (TiO$_2$)

50.0 parts by weight of levelling agent masterbatch 65.0 parts by weight of crosslinking agent according to I.21

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ≮ | MEK Resistance |
| 15 | 200 | 50–60 | 111 | 115.2 | 5.5–5.9 | 0 | 21 | 80 |
| 20 |  | 50–60 | 111 | 230.4 | 5.7–6.3 | 0 | 20 | 100 |
| 25 |  | 60–70 | 111 | 230.4 | 6.0–6.7 | 0 | 23 | 120 |
| 30 | 180 | 60–70 | 100 | 115.2 | 4.7–5.1 | 0 | 25 | 60 |

EXAMPLE 27

In accordance with the method described, the powder coating having the following formulation was produced, applied and baked at between 170° C. and 220° C.

475.0 parts by weight of epoxide according to II.1

75.0 parts by weight of crosslinking agent according to I.21

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ≮ | MEK Resistance |
| 10 | 220 | 45–55 | 100 | 115.2 | 5.0–5.3 |  | 9 | 80 |
| 15 | 200 | 50 | 100 | 115.2 | 6.0–6.2 | 0 | 8 | 80 |
| 20 |  | 40–50 | 111 | 230.4 | 6.8 | 0 | 8 | 90 |
| 25 |  | 50–65 | 100 | 345.6 | 5.8–5.9 | 0 | 8 | 90 |
| 20 | 180 | 65 | 100 | <115.2 | 4.1–4.4 | 0 | 11 | 70 |
| 25 |  | 60–70 | 100 | 115.2 | 4.7–4.9 | 0 | 10 | 80 |
| 30 | 170 | 50–60 | 100 | <115.2 | 3.5–4.1 | 0 | 10 | 60 |

EXAMPLE 28

In accordance with the method described, the powder coating having the following formulation was produced, applied and baked at between 180° C. and 200° C.

485.0 parts by weight of epoxide according to II.1

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 20 | 200 | 45–60 | 100 | 230.4 | 5.1–6.1 | 0 | 10 | 24 |
| 25 | | 50–70 | 125 | 230.4 | 5.4–6.0 | 0 | 10 | 28 |
| 30 | | 70 | 125 | 345.6 | 5.3–6.2 | 0 | 10 | 30 |
| 25 | 180 | 60–80 | 100 | 115.2 | 3.5–4.2 | 0 | 12 | 20 |
| 30 | | 60 | 100 | 115.2 | 4.6–5.0 | 0 | 12 | 28 |

EXAMPLE 29

In accordance with the method described, the powder coating having the following formulation was produced, applied and baked at between 200° C. and 170° C.

215.0 parts by weight of epoxide according to II.1

260.0 parts by weight of epoxide according to II.2

75.0 parts by weight of crosslinking agent according to I.21

400.0 parts by weight of white pigment ($TiO_2$)

50.0 parts by weight of levelling agent masterbatch 500.0 parts by weight of epoxide according to II.1

50.0 parts by weight of crosslinking agent according to I.25

400.0 parts by weight of white pigment ($TiO_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 15 | 200 | 60–70 | 111 | 115.2 | 5.9–6.3 | 0 | 9 | 76 |
| 20 | | 55–70 | 111 | 230.4 | 6.3–6.5 | 0 | 10 | 88 |
| 25 | | 50–60 | 100 | 230.4 | 6.0–6.7 | 0 | 9 | 92 |
| 20 | 180 | 50–60 | 111 | <115.2 | 3.9–4.4 | 0 | 10 | 66 |
| 25 | | 60 | 111 | 115.2 | 4.2–4.8 | 0 | 11 | 78 |
| 30 | 170 | 50–60 | 100 | <115.2 | 3.4–3.9 | 0 | 10 | 62 |

EXAMPLE 30

In accordance with the method described, the powder coating having the following formulation was produced, applied and baked at 200° C.

480.0 parts by weight of epoxide according to II.1

70.0 parts by weight of crosslinking agent according to I.23

400.0 parts by weight of white pigment ($TiO_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ∢ | MEK Resistance |
| 12 | 200 | 60 | 111 | <115.2 | 6.0–6.4 | 0 | 17 | 6 |
| 15 | | 45–55 | 111 | 115.2 | 5.3–6.5 | 0 | 19 | 10 |
| 20 | | 60–70 | 111 | 230.4 | 7.4–7.5 | 0 | 20 | 16 |

EXAMPLE 31

In accordance with the method described, the powder coating having the following formulation was produced, applied and baked at between 200° C. and 180° C.

| Baking Conditions | | Mechanical Characteristics | | | | | Solvent resistance |
|---|---|---|---|---|---|---|---|
| Time/ min | Temp. °C. | LT | HB | Imp. rev. | EI | CH | GG 60° ≮ | MEK Resistance |
| 15 | 200 | 50–60 | 111 | 115.2 | 5.3–5.8 | 0 | 34 | 20 |
| 20 | | 50–65 | 111 | 115.2 | 5.6–6.2 | 0 | 36 | 40 |
| 25 | | 55–65 | 125 | 230.4 | 6.3–6.7 | 0 | 35 | 60 |
| 30 | 180 | 60 | 111 | 115.2 | 5.0–5.5 | 0 | 36 | 30 |

EXAMPLE 32

In accordance with the method described, the powder coating having the following formulation was produced, applied and baked at between 200° C. and 180° C.

490.0 parts by weight of epoxide according to II.1

60.0 parts by weight of crosslinking agent according to I.25

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ≮ | MEK Resistance |
| 15 | 200 | 50 | 125 | 115.2 | 6.4–6.5 | 0 | 37 | 80 |
| 20 | | 55–60 | 125 | 230.4 | 6.4–6.9 | 0 | 37 | 80 |
| 25 | | 50–60 | 125 | 230.4 | 7.6–8.8 | 0 | 36 | 110 |
| 25 | 180 | 50–65 | 111 | 115.2 | 5.2–5.7 | 0 | 34 | 30 |
| 30 | | 45–55 | 125 | 115.2 | 6.0–6.3 | 0 | 36 | 60 |

EXAMPLE 33

In accordance with the method described, the powder coating having the following formulation was produced, applied and baked at between 200° C. and 180° C.

480.0 parts by weight of epoxide according to II.1

70.0 parts by weight of crosslinking agent according to I.25

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ≮ | MEK Resistance |
| 15 | 200 | 60 | 125 | 115.2 | 5.5–5.8 | 0 | 38 | 20 |
| 20 | | 50–65 | 125 | 230.4 | 6.2–6.6 | 0 | 41 | 100 |
| 25 | | 50–60 | 125 | 345.6 | 6.7–7.6 | 0 | 41 | >200 |
| 25 | 180 | 55–60 | 125 | 115.2 | 4.8–5.2 | 0 | 40 | 30 |
| 30 | | 50–60 | 125 | 230.4 | 5.5–5.9 | 0 | 42 | 70 |

IV. Carboxyl group-containing polyester

For the production of hybrid powder coatings, the carboxyl group-containing polyester described below was employed, having the following characteristics (manufacturer's data):

| | |
|---|---|
| Acid number | 52–58 mg of KOH/g |
| Melting range | 104–106° C. |
| Glass transition temperature | about 58° C. |
| Viscosity at 185° C. | 33,400 mPa.s |

V. Hybrid powder coatings

The processing of the raw materials, the preparation and application are carried out in analogy to III.

EXAMPLE 1

350.0 parts by weight of epoxide according to II.1

145.0 parts by weight of polyester according to IV 55.0 parts by weight of crosslinking agent according to I.1

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ≮ | MEK Resistance |
| 10 | 200 | 80 | 111 | 115.2 | 5.7–6.5 | 0 | 51 | 24 |
| 15 | | 70–80 | 111 | 115.2 | 6.2–6.6 | 0 | 51 | 32 |
| 20 | | 60–70 | 111 | 115.2 | 5.7–6.8 | 0 | 50 | 36 |
| 20 | 180 | 70–80 | 125 | 115.2 | 4.7–5.6 | 0 | 51 | 22 |
| 30 | | 50–60 | 125 | 115.2 | 5.5–6.8 | 0 | 48 | 28 |
| 30 | 170 | 50–60 | 111 | 115.2 | 5.0–5.6 | 0 | 48 | 10 |

EXAMPLE 2

In accordance with the method described, the powder coating having the following formulation was produced, applied and baked at between 180° C. and 200° C.

390.0 parts by weight of epoxide according to II.1

75.0 parts by weight of crosslinking agent according to I.1

400.0 parts by weight of white pigment (TiO$_2$)

50.0 parts by weight of levelling agent masterbatch 85.0 parts by weight of polyester according to V 390.0 parts by weight of epoxide according to II.1

75.0 parts by weight of crosslinking agent according to I.16

400.0 parts by weight of white pigment (TiO$_2$)

50.0 parts by weight of levelling agent masterbatch 85.0 parts by weight of polyester according to IV

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ≮ | MEK Resistance |
| 10 | 200 | 65–80 | 125 | 115.2 | 3.8–4.2 | 0 | 43 | 28 |
| 15 | | 60–65 | 125 | 115.2 | 5.6–5.7 | 0 | 43 | 46 |
| 20 | | 60 | 125 | 115.2 | 4.9–5.3 | 0 | 40 | 54 |
| 20 | 180 | 70–80 | 125 | 115.2 | 3.7–4.2 | 0 | 47 | 20 |
| 30 | | 60–70 | 125 | 115.2 | 4.0–4.5 | 0 | 49 | 28 |

EXAMPLE 3

In accordance with the method described, the powder coating having the following formulation was produced, applied and baked at between 200° C. and 180° C.

145.0 parts by weight of polyester according to IV 350.0 parts by weight of epoxide according to II.1

55.0 parts by weight of crosslinking agent according to I.11

400.0 parts by weight of white pigment (TiO$_2$)

50.0 parts by weight of levelling agent masterbatch

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° ≮ | MEK Resistance |
| 12 | 200 | 60–70 | 111 | 115.2 | 5.3–5.7 | 0 | 45 | 20 |
| 15 | | 60 | 125 | 115.2 | 5.6–6.4 | 0 | 48 | 24 |
| 20 | | 60–75 | 111 | 230.4 | 5.9–6.6 | 0 | 50 | 28 |
| 20 | 180 | 50–70 | 111 | 115.2 | 4.3–5.0 | 0 | 46 | 18 |
| 30 | | 60–70 | 125 | 115.2 | 4.7–5.5 | 0 | 48 | 22 |

EXAMPLE 4

In accordance with the method described, the powder coating having the following formulation was produced, applied and baked at between 200° C. and 180° C.

| Baking Conditions | | Mechanical Characteristics | | | | | Solvent resistance | |
|---|---|---|---|---|---|---|---|---|
| Time/ min | Temp. °C. | LT | HB | Imp. rev. | EI | CH | GG 60° ⊀ | MEK Resistance |
| 10 | 200 | 60–65 | 100 | 115.2 | 5.8–6.2 | 0 | 34 | 20 |
| 15 | | 60 | 111 | 230.4 | 5.2–6.0 | 0 | 36 | 26 |
| 20 | | 60–70 | 100 | 345.6 | 6.9–7.5 | 0 | 32 | 28 |
| 30 | 180 | 50–60 | 100 | 230.4 | 3.7–4.2 | 0 | 40 | 14 |

EXAMPLE 5

In accordance with the method described, the powder coating having the following formulation was produced, applied and baked at between 180° C. and 200° C.

390.0 parts by weight of epoxide according to II.1
75.0 parts by weight of crosslinking agent according to I.18
400.0 parts by weight of white pigment (TiO₂)
50.0 parts by weight of levelling agent masterbatch
85.0 parts by weight of polyester according to IV
65.0 parts by weight of crosslinking agent according to I.25
400.0 parts by weight of white pigment (TiO₂)
50.0 parts by weight of levelling agent masterbatch
105.0 parts by weight of polyester according to IV

| Baking Conditions | | Mechanical Characteristics | | | | | Solvent resistance | |
|---|---|---|---|---|---|---|---|---|
| Time/ min | Temp. °C. | LT | HB | Imp. rev. | EI | CH | GG 60° ⊀ | MEK Resistance |
| 10 | 200 | 50–60 | 111 | 345.6 | 6.0 | 0 | 23 | 20 |
| 15 | | 80–90 | 125 | 230.4 | 5.3–6.1 | 0 | 19 | 24 |
| 20 | | 50–60 | 125 | 691.2 | 7.1–7.3 | 0 | 19 | 30 |
| 20 | 180 | 70–75 | 111 | 115.2 | 2.5–2.9 | 0 | 22 | 10 |
| 30 | | 50–70 | 125 | 230.4 | 3.5–4.0 | 0 | 20 | 14 |

EXAMPLE 6

In accordance with the method described, the powder coating having the following formulation was produced, applied and baked at between 180° C. and 200° C.

390.0 parts by weight of epoxide according to II.1
75.0 parts by weight of crosslinking agent according to I.21
400.0 parts by weight of white pigment (TiO₂)
50.0 parts by weight of levelling agent masterbatch
85.0 parts by weight of polyester according to IV

| Baking Conditions | | Mechanical Characteristics | | | | | Solvent resistance | |
|---|---|---|---|---|---|---|---|---|
| Time/ min | Temp. °C. | LT | HB | Imp. rev. | EI | CH | GG 60° ⊀ | MEK Resistance |
| 10 | 200 | 80–100 | 111 | <115.2 | 4.0 | 0 | 11 | 50 |
| 15 | | 70–80 | 111 | 115.2 | 5.3–5.6 | 0 | 15 | 80 |
| 20 | | 60–70 | 111 | 230.4 | 5.3–5.9 | 0 | 12 | 110 |
| 20 | 180 | 80–100 | 100 | <115.2 | 3.2–3.4 | 0 | 11 | 30 |
| 30 | | 70–80 | 111 | 115.2 | 4.1–4.4 | 0 | 11 | 40 |

EXAMPLE 7

In accordance with the method described, the powder coating having the following formulation was produced, applied and baked at between 200° C. and 180° C.

380.0 parts by weight of epoxide according to II.1

| Baking Conditions | | Mechanical Characteristics | | | | | | Solvent resistance |
|---|---|---|---|---|---|---|---|---|
| Time/ min | Temp. °C. | LT | HB | Imp. rev. | EI | CH | GG 60° < | MEK Resistance |
| 15 | 200 | 50–60 | 111 | <115.2 | 4.3–4.5 | 0 | 34 | 20 |
| 20 | | 60 | 100 | 115.2 | 4.7–5.1 | 0 | 38 | 30 |
| 25 | | 55–65 | 111 | 230.4 | 5.3–5.8 | 0 | 37 | 46 |
| 30 | 180 | 50–60 | 100 | <115.2 | 4.4–4.9 | 0 | 40 | 34 |

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A salt of pyromellitic acid with an amine of the formula (A):

$$R_1 - N - R_2 \atop R_3 \qquad (A)$$

wherein $R_1$, $R_2$ and $R_3$, identical or different, are $C_{1-20}$ aliphatic, $C_{3-20}$ cycloaliphatic, $C_{5-20}$ araliphatic or $C_{5-20}$ aromatic hydrocarbon radicals or mixtures thereof;

wherein one or more $CH_2$ groups in the carbon chain can be replaced by O atoms or by $NR_4$ where $R_4$ is $C_{1-6}$-alkyl, and wherein one or more terminal methyl groups can be replaced by dialkyl-substituted amino groups having 1 to 6 carbon atoms;

or wherein $R_1$ and $R_2$ may form a joint ring in which a $CH_2$ group may be replaced by an O atom or by an $NR_4$ group, or wherein $R_1$, $R_2$ and $R_3$ are each $-CH_2-CH_2-$ and are each attached by way of the valance bond not joined to the N atom of formula (A) to a common N atom.

2. A process for preparing a salt of pyromellitic acid which consists essentially in reacting pyromellitic acid with an amine of the formula (A) in the ratio of 1 mol of pyromellitic acid with 0.5 to 2 mol of the amine, wherein formula (A) is:

$$A)\ R_1 - N - R_2 \atop R_3$$

wherein in (A) $R_1$, $R_2$ and $R_3$, identical or different, are $C_{1-20}$ aliphatic, $C_{3-20}$ cycloaliphatic, $C_{5-20}$ araliphatic or $C_{5-20}$ aromatic hydrocarbon radicals or mixtures thereof;

wherein one or more $CH_2$ groups in the carbon chain can be replaced by O atoms or by $NR_4$ wherein $R_4$ is $C_{1-6}$-alkyl, and wherein one or more terminal methyl groups can be replaced by dialkyl-substituted amino groups having 1 to 6 carbon atoms;

or wherein $R_1$ and $R_2$ may form a joint ring in which a $CH_2$ group may be replaced by an O atom or by an $NR_4$ group, or wherein $R_1$, $R_2$ and $R_3$ are each $-CH_2-CH_2-$ and are attached by way of the valance bond not joined to the N atom of formula (A) to a common N atom;

in a solvent which is $H_2O$ or ethanol, or a mixture thereof at 50° C. to 100° C; and after reaction has finished, isolating said salt of pyromellitic acid from said solvent.

* * * * *